United States Patent
Quan et al.

(10) Patent No.: US 6,585,963 B1
(45) Date of Patent: Jul. 1, 2003

(54) NAIL COMPOSITIONS AND METHODS OF ADMINISTERING SAME

(75) Inventors: Danyi Quan, Salt Lake, UT (US); Ana Ruiz, Roy, UT (US)

(73) Assignee: Watson Pharmaceuticals, Inc., Corona, CA (US)

(*) Notice: Subject to any disclaimer, the term of this patent is extended or adjusted under 35 U.S.C. 154(b) by 0 days.

(21) Appl. No.: 09/832,349

(22) Filed: Apr. 10, 2001

Related U.S. Application Data

(63) Continuation of application No. 09/784,635, filed on Feb. 15, 2001.

(51) Int. Cl.[7] ............................. A61K 7/04; A61K 9/70; A61F 13/00
(52) U.S. Cl. ........................ 424/61; 424/443; 514/946
(58) Field of Search .................... 424/61, 401, 404, 424/443; 514/946

(56) References Cited

U.S. PATENT DOCUMENTS

| | | | | |
|---|---|---|---|---|
| 5,023,252 A | | 6/1991 | Hseih | 514/183 |
| 5,264,206 A | * | 11/1993 | Bohn et al. | 424/61 |
| 5,601,839 A | * | 2/1997 | Quan et al. | 424/448 |
| 6,231,875 B1 | * | 5/2001 | Sun et al. | 424/401 |

* cited by examiner

*Primary Examiner*—Thurman K. Page
*Assistant Examiner*—S. Howard
(74) *Attorney, Agent, or Firm*—Thorpe North & Western, LLP

(57) ABSTRACT

Nail compositions and methods of use thereof are disclosed. Additionally, nail kits comprising a nail composition and pre-treatment compositions are disclosed. Further, supportive devices such as bandages for use in the administering a nail composition are disclosed. In one aspect of the invention, the nail compositions comprise an antifungal agent, including fluconazole, a non-cellulosic polymeric carrier, and an enhancer, while being substantially free of urea, sulfhydryl-containing amino acids, or vasodilators.

22 Claims, No Drawings

NAIL COMPOSITIONS AND METHODS OF ADMINISTERING SAME

CROSS-REFERENCE TO RELATED APPLICATIONS

This application is a continuation of application Ser. No. 09/784,635 filed Feb. 15, 2001.

FIELD OF THE INVENTION

The present invention relates generally to nail compositions and methods of administering such compositions. Accordingly, this invention covers the fields of pharmaceutical sciences, medicine, cosmetics, and related sciences.

BACKGROUND OF THE INVENTION

The health and overall physical appearance of fingernails and toenails may affect a person's ability to perform certain tasks, as well as their desire to engage in certain activities.

Unhealthy nails may be attributed to a variety of conditions, such as bacterial infection, improper grooming, neglect, and aging. Unhealthy nails may also be caused by fungal infections such as onychomycosis, a condition recognized by discoloration beneath toenails and fingernails along with pain when pressure is placed near or at the site of discoloration.

The disadvantage of systemic drug administration to treat localized peripheral conditions such as nail diseases are well known to include general ineffectiveness, and impact on other bodily systems. Because of ease in administration and comfort, topical treatments that treat nail conditions by imparting an active agent through the nail to the nail bed and other surrounding tissues are highly preferable to oral administration or to surgery.

Human nails, however, with respect to chemical composition and permeability, are more like hair than to stratum corneum of the skin. Nitrogen is the major component of the nail attesting to the nail's proteinaceous nature. The total lipid content of mature nail is 0.1 to 1.0%, while the skin stratum corneum lipid is about 10% w/w, and the level of hydration of the nail is considerably lower than the stratum corneum. The nail plate is about 100–200 times thicker than the stratum corneum and has a very high affinity for and capacity for binding and retaining many drugs. In fact, topical nail therapy has generally been ineffective for many conditions.

The nail plate is therefore too thick and too dense for a drug to penetrate at a practical rate. Although nail is similar to stratum corneum of the skin in that it is derived from epidermis, it is mainly composed of hard keratin (highly disulfide-linked) and is approximately 100-fold thicker than strateum corneum. For this reason, in order to deliver a sufficient amount of a drug into the nail plate, the permeability of the nail plate to the drug needs to be enhanced.

Several enhancers have been taught in the prior art to overcome the presence of high sulfide bonds in the nail plate. These enhancers include kerolytic agents such as urea and salicylic acid, to soften the nail plates, as disclosed in Konno et al. (EP 152281) and Sun et al. (U.S. Pat. No. 5,696,164), and reducing agents such as cysteine and its derivatives, which can break the disulfide bonds in keratin to increase the ability of the nail to hydrate, as disclosed in Olthoff et al. (EP 440298) and Sun et al. (U.S. Pat. No. 6,042,845). The prior art also teaches combining kerolytic agents and reducing agents to improve nail penetration.

Other reducing agents such as ammonium thioglycolate are also taught in the prior art. Puri (WO 86/00013) discloses that the condition of hair, skin and nails is improved by treatment with an aqueous ammonium thioglycolate solution, followed by treatment with a protein hydrolyzate. Rothman (WO 89/070793) discloses a protein-containing composition comprising reducing agents such as ammonium thioglycolate for treating kerotinous tissues.

Compounds with vasodilating action are also taught by the prior art. Bohn et al. (U.S. Pat. No. 6,007,798) discloses a nail varnish comprising a compound having a vasodilator action and a water-insoluble film-forming agent for treating growth disturbances of the nail.

Most of the inventions, as described above, have not been commercially successful. It is believed that compositions and methods for enhancing penetration of a nail agent and methods for treating nail conditions according to the present invention would be a significant advancement in the art.

SUMMARY OF THE INVENTION

The present invention provides nail compositions comprising a non-cellulosic polymeric carrier, a nail agent and an enhancer. These compositions are free of urea, sulfhydryl-containing amino acids, and vasodilators.

The present invention also provides methods for enhancing nail penetration of a nail agent using an enhancer of the present invention.

The present invention also provides methods of treatment of a nail condition comprising applying to the affected nails a nail composition of the present invention.

In one aspect of the present invention, the nail agent may include substances such as drugs, cosmetics, cosmeceuticals, or any mixtures thereof.

In a further aspect of the present invention, the nail agent is a drug, which is an azole, an allyl compound, or any combinations thereof.

In one aspect of the present invention, the composition may be in the form of a liquid, a solution, a suspension, a varnish, or a lacquer.

In another aspect of the present invention, the enhancer used in the composition may include, but not limited thereto, triacetin, lauramide diethanolamine, 1,8-epoxy-p-menthane, caproic triglyceride, cineole, dimethylsulfoxide (DMSO), dimethyl formamide (DMF), N,N-dimethylacetamide (DMA), propylene glycol, sorbitan, sorbitan monooleate, and N-methyl pyrrolidone, and any mixtures thereof.

In another aspect of the present invention, the non-cellulosic polymeric carrier may be a vinyl polymer or copolymer, including vinyl acetate and vinyl acetate copolymers, and vinyl ether polymers and copolymers.

In a further aspect of the invention, the polymeric carrier may be a copolymer of methylvinyl ether and maleic anhydride or a copolymer of methylvinyl ether and maleic acid.

The present invention also provides a nail composition as described herein that may be directly applied or used in connection with a bandage, which is adapted to topically administer the composition.

The present invention also provides a composition which may be used as a component of a nail kit, or a nail treatment kit, which may also include a pre-treatment composition comprising an enhancer of the present invention, including but not limited thereto propylene glycol, sorbitan monooleate, and N-methyl pyrrolidone, or any mixtures thereof.

There has thus been outlined, rather broadly, various features of the invention so that the detailed description thereof that follows may be better understood, and so that the present contribution to the art may be better appreciated. Other features of the present invention will become clearer from the following detailed description of the invention, taken with the accompanying claims, or may be learned by practice of the invention.

DETAILED DESCRIPTION

Definitions

Before the composition and methods are disclosed and described herein, it is understood that this invention is not limited to the particular process steps and materials disclosed herein, but is extended to the equivalents thereof as would be recognized by those ordinarily skilled in the relevant arts. It should be understood that the terminology employed herein is used for the purpose of describing particular embodiments only and is not intended to limit the scope of the invention.

In describing and claiming the present invention, the following terminology will be used.

The singular forms "a," "an," and "the" include plural referents unless the context clearly dictates otherwise. Thus, for example, reference to "a drug" includes reference to one or more drugs, and reference to "an enhancer" includes reference to one or more of such enhancers.

The term "formulation" and "composition" may be used interchangeably herein.

The term "nail agent" refers to an agent, which exerts a desirable effect on a nail condition. The desirable effect may be a reduction of symptoms of a nail disease or condition, or treatment or cure, or both, of a nail disease or condition, or improving the appearance of a nail. Examples of nail agents include, but not limited thereto, drugs, cosmetics, and cosmeticeuticals.

The terms "pharmaceutical" and "drug" may be used interchangeably and refer to a nail agent with pharmacological activity or activities. These terms are well known in the pharmaceutical and medicinal arts.

The terms "cosmetic" and "cosmetic agent" may be used interchangeably and refer to a nail agent which exerts a positive, or beautifying effect upon the appearance of a nail and the surrounding tissue.

The terms "cosmeticeutical" and "cosmeticeutical agent" may be used interchangeably and refer to a nail agent which achieves appositive, or beautifying effect upon the appearance of a nail and its surrounding tissues by imparting a beneficial action which improves the health of the nail and the surrounding tissues.

It is appreciated that the terms "pharmaceutical," "cosmetic" and "cosmeticeutical" may be overlapping in some cases. For example, vitamin E, which has been used as a cosmetic, has some pharmacological activity.

The term "biologics" refers to a biological product, including, but not limited to, those products subject to licensure under the U.S. Public Health Service Act, which is any virus, therapeutic serum, toxin, antitoxin, vaccine, blood, blood component or derivative, allergenic product, or analogous product, applicable to the prevention, treatment or cure of diseases or injuries to humans. Biological products include, but are not limited to, bacterial and viral vaccines, human blood and plasma and their derivatives, and certain products produced by biotechnology, such as interferons and erythropoietins. Biological products also include direct gene products, e.g., a protein or a polypeptide, or an indirect gene product, e.g., a polysaccharide, an amino acid, a lipid, etc., made by fermentation of a microorganism and recovered therefrom. The microorganism may be a conventional, established strain or culture or cell line, or one that is made by recombinant DNA technology.

The term "nail flux" refers to the rate at which a nail agent penetrates through a nail.

The terms "nail" and "nail plate" may be used interchangeably, and refer to the horny cutaneous plate (stratum corneum unguis) on the dorsal surface of the distal end of a finger or a toe. It should be understood that since a nail is not often attached to the underlying skin and at the cuticles any administration of a nail composition to a nail or a nail plate may thus include administration to such attached skin and cuticles.

The phrase "non-cellulosic polymeric carrier" refers to a polymeric substance that is substantially free of cellulose or cellulose derivatives. Examples of cellulose and cellulose derivatives include, but not limited thereto, methylcellulose, ethylcellulose, hydroxypropylcellulose, hydroxymethylcellulose, hydroxymethylethylcellulose, hydroxyethylmethylcellulose, hydroxypropylmethylcellulose, nitrocellulose, and carboxymethylcellulose.

The terms "enhancement" or "permeation enhancement" may be used interchangeably and refer to an increase in the nail flux of a nail agent. Thus, "permeation enhancer" or "penetration enhancer," or simply, "enhancer" refers to an agent, or a mixture of agents, that achieves such permeation enhancement. Several compounds have been investigated for use as penetration enhancers. See, for example, U.S. Pat. Nos.: 5,601,839; 5,006,342; 4,973,468; 4,820,720; 4,006,218; 3,55.1,154; and 3,472,931. Furthermore, an index of skin permeation enhancers is disclosed on the Internet by David W. Osborne and Jill J. Hinke, titled, "Skin Enhancers Cited in the Technical Literature," at http://www.pharmtech.com/technical/osborne/osborne.htm, incorporated herein by reference in its entirety.

In one aspect, the increase in permeation is measured by comparing a formulation that has no enhancer to one that is of a different kind or in a different concentration. General methods for measuring penetration enhancement are well known in the art. See, for example, Merritt et al., "Diffusion Apparatus for Skin Penetration," *Journal of Controlled Release*, 61 (1984), incorporated herein by reference in its entirely. See also U.S. Pat. Nos. 4,863,970; 4,888,354; 5,164,190; and 5,834,010; which are incorporated by reference in their entirety.

See, also, the following literature publications:

Mertin and Lippold, "In vitro Permeability of the Human Nail and of a Keratin Membrane from Bovine Hooves: Prediction of the Penetration Rate of antimycotics through the Nail Plate and Their Efficacy," *Journal of Pharm. Pharmacol.* 49(9):866–872 (1997).

Mertin and Lippold, "In vitro Permeability of the Human Nail and of a Keratin Membrane from Bovine Hooves: Penetration of Chloramphenicol from Lipophilic Vehicles and a Nail lacquer," *Journal of Pharm. Pharmacol.* 49(3):241–245 (1997).

Mertin and Lippold, "In vitro Permeability of the Human Nail and of a Keratin Membrane from Bovine Hooves: Influence of a Partition Coefficient Octanol/Water and the Water Solubility of Drugs on their Permeability and Maximum Flux," *Journal of Pharm. Pharmacol.* 49(1):30–34 (1997).

Walters, Flynn and Marvel, "Physical Characterization of the Human Nail: Solvent Effects on the Permeation of Homologous Alcohols," *Journal of Pharm. Pharmacol.* 37(11):771–775 (1985).

Walters, Flynn and Marvel, "Penetration of the Human Nail Plate: The Effects of Vehicle pH on the Permeation of Miconazole," *Journal of Pharm. Pharmacol.* 37(7):498–499 (1985).

Walters, Flynn and Marvel, "Physical Characterization of the Human Nail: Permeatin Patterns for Water and the Homologous Alcohols and Differences with Respect to the Stratum Corneum," *Journal of Pharm. Pharmacol.* 35(1):28–33 (1983).

The term "plasticizer" refers to an agent that may aid the liberation of a nail agent from a carrier or a polymeric matrix. A plasticizer may or may not play a role in enhancing the flux of a nail agent. It is possible that a specific compound may act as a plasticizer, or as an enhancer, depending on its use concentration.

The term "effective amount" of an enhancer means an amount effective to increase, to a selected degree, the flux rate of a nail agent through the nail. Methods for assaying the effective amount and other characteristics of permeation enhancers are well known in the art. See, for example, Merritt et al. supra. See, also, the following literature publications:

Mertin and Lippold, "In vitro Permeability or the Human Nail and of a Keratin Membrane from Bovine Hooves: Prediction of the Penetration Rate of Antimycotics through the Nail Plate and Their Efficacy," *Journal of Pharm. Pharmacol.* 49(9):866–872 (1997).

Walter, Flynn and Marvel, "Physical Characterization of the Human Nail: Solvent Effects on the Permeation of Homologous Alcohols," *Journal of Pharm. Pharmacol.* 37(11):771–775 (1985).

Kobayashi, Miyamoto, Sugibayashi and Morimoto, "Enhancing Effect of N-acetyl-1-cysteine or 2-mercaptoethanol on the in vitro Permeation of 5-fluorouracil or Tolnaftate through the Human Nail Plate," *Chem. Pharm. Bull.* (Tokyo), 46(11): 1797–1802 (1998).

The phrases "therapeutically effective amount" and "cosmetically effective amount" refer to an amount of a nail agent sufficient to achieve therapeutic or cosmetic results in the treatment of a nail condition for which the nail agent is expected to be effective. The determination of an effective amount is well within the ordinary skill in the art of pharmaceutical, cosmetic, and medical sciences. See, for example, Meiner and Tonascia, "Clinical Trials: Design, Conduct, and Analysis," *Monographs in Epidemiology and Biostatistics, Vol.* 8 (1986), incorporated by reference in its entirety.

The phrase "substantially free" refers to the absence of a specific agent or compound, or if present, such agent or compound is present in an amount that does not provide its functional benefit to a measurable degree. For example, a composition that is said to be substantially free of urea may be either completely devoid of urea, or may contain a residual amount of urea that does not provide an intended technical effect or an intended functional benefit, such as an increase in flux rate of a nail agent to a measurable degree.

The term "vasodilator" refers to those agents that cause relaxation of peripheral blood vessels. Several of such agents are known in the pharmaceutical arts, e.g., nitroglycerin, isoborbide, nifedipine, etc.

The phrases "nail disease" and "nail condition" may be used interchangeably and refer to a condition of the nail or its surrounding tissue Which produces signs or symptoms of abnormality. Examples of such diseases and conditions range from infections, such as fungal and bacterial, to cancerous conditions, to inflammation and aesthetic conditions, such as discoloration.

Some specific diseases include onychomycosis, paronychia, nail psoriasis, etc. Onychomycosis includes white, black, distal, proximal, superficial, or total dystrophic onychomycosis, or a combination thereof. Paronychia includes bacterial, fungal, and drug-inducted types. Other fungal infections include sporotrichosis, chromoblastomycosis, coccidioidomycosis and blastomycosis. Viral infections include paravaccinia virus and herpes infections such as herpes simplex and herpes xoster.

Additional diseases treatable according to the present invention include, but not limited thereto, gonorrhea, syphillis, pinta, leprosy, Leishmaniasis, Trichinosis, scabies, pediculosis, tungiasis, Larva migrans, subungual myasis, impetigo, Veillonella, Staphylococcal, and blistering distal dactylitis.

These infections may be caused by, inter alia, fungi such as Trichophyton, bacteria such as Pseudomonas, Clostridia, Mycobacterium, Pasteurella, yeasts such as Candida, moulds such as Acremonium, Fusarium, Aspergillus, Penicillium, Scopulariopsis, Hendersonula, Scytalidium, etc.

In addition to the diseases and conditions of a nail, several systemic conditions and diseases may also have impact on the nail. For example, rheumatoid arthritis, HIV infections, immunological disorders such as Graft-versus-host disease (GVHD), malaria, Kawasaki disease, diphtheria, anemias, hereditary conditions, systemic neoplastic diseases such lungcarcinoma, breast carcinoma, lymphormas, and Hodgkin's disease. Furthermore, systemic drugs such as phenothiazines, lithium, tetracyclines, quinolones and beta-blockers may also have adverse effects on the nails.

Tumors of the nail apparatus include: epithelial tumors, such as warts, actinitic keratosis, basal cell carcinoma; soft tissue tumors such as fibrous tumors, vascular tumors, Kaposi sarcoma, Merkel cell tumor, tumors of peripheral nerves, osteocartilaginous tumors, chondrosarcoma, lipomatous tumors; degenerative tumors such as myxoma, sublingual calcification; hystiocytic and metastatic processes, and melanocytic lesions.

Additional nail conditions that may be treatable using the present invention include discoloration of the nail, onycholysis, granulatino, contact dermatitis, hyperonychia, keratitis, and Leuconychia.

The term "administration" refers to delivering a nail agent to a nail surface. Administration may comprises of applying, rolling, dropping, rubbing, dabbing, brushing, painting, putting, placing, taping, pressing, etc., of a nail composition of the present invention to a nail surface. These and other methods of administration are well known to those in the pharmaceutical arts.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited.

As an illustration, a concentration range of "about 1% w/w/to about 4.5% w/w" should be interpreted to include not only the explicitly recited concentration of about 1% to about 4.5% w/w, but also include individual concentrations and the sub-ranges within the indicated range. Thus, included in this numerical range are individual concentrations such as 2% w/w, 3% w/w, and 4% w/w, and sub-ranges such as from 1% w/w to 3% w/w, from 2% w/w to 4% w/w, etc.

The same principle applies to ranges reciting only one numerical value. For example, a range recited as "less than about 4.5% w/w" should be interpreted to include all of the values and ranges as elaborated above for the range of "from about 1% w/w to about 4.5% w/w." Furthermore, such an interpretation should apply regardless of the breadth of the range or the characteristics being described.

Nail Agents

As aforementioned, the present invention may be used to administer a wide variety of nail agents, including drugs, cosmetics, and cosmeceuticals. One of the ordinary skill in the art would appreciate that practically any type of drugs, cosmetics, or cosmeticeuticals, is a suitable candidate for delivery in accordance with the present invention.

In general, the drugs that are used in the present invention include therapeutic agents which ameliorate or prevent the various disease states which typically afflict a nail. These drugs include, but not being limited thereto, antibiotics (including antimicrobials, antibacterials, antimycobacterials, antiamebics, and, anfungals), antineoplastic agents, anticancer agents, antipsoriatics, agents that affect immune response such as anti-inflammatories (including steroidal and non-steroidal anti-inflammatory agents), and mixtures or combinations thereof.

Examples of specific drugs include, without limitation: antibiotics, which include amoxicillin, cloxacillin sodium, penicillin G potassium; antimicrobials, which include benzalkonium chloride, chlorohexidine, gluconate hexachlorophene; antibacterials, which include sulfabenzamide, sulfadiazine, sulfasalazine; antimycobacterials, which include chlofazimine, ethambutol, isoniazid; antiamebics, which include arsthinol, bialamicol, carbarsone; and anthelmimics, which include ivermectin, bithionol, and piperazine.

Examples of antifungal agents include, without limitation: azoles, allylamines, morpholines, polyenes, and other agents.

Examples for azole compounds include imidazoles and triazoles. Examples for imidazoles include, but not limited thereto, ketoconazole, miconazole, bifonazole, butoconazole, clotrimazole, croconazole, eberconazole, econazole, fenticonazole, flutimazole, isoconazole, ketoconazole, lanoconazole, neticonazole, omoconazole, oxiconazole, setraconazole, sulconazole, and tioconazole. Examples for triazoles include fluconazole, itraconazole, and terconazole.

Examples for allylamine compounds include terbinafine and natrifine. Examples for morphonlines include amorolfine. Examples for polyenes include amphotericin B, nystatin, and natamaycin. Examples for other antifungal agents include flucytosine, griseofulvin, potassium iodide, butenafine, ciclopirox, ciloquinol (iodochlorhydroxyquin), haloprogin, tolnaftate, aluminum chloride 30%, Catellant's paint, compound undecylenic acid, gentian violet, oil of bitter orange, potassium permanganate, propylene glycol (50% in water), selenium sulphide. (2.5% lotion), solution plus salicylic acid, Whitfield's ointment, and zinc pyruthione.

Further examples, for antifungal, include griseofulvin; for anti-neoplastic agents, include adriamycine, cyclophosphamide, methotrexate; for anticancer agents, include paclitaxel, N-[[(substituted phenyl)amino]carbonyl] alkylsulfonamides; for antipsoriatics, include coal tar, flurandrenolide, and dithranol; for immune response steroidal anti-inflammatory agents, include hydrocortisone, dioxyanthranol, and betamethasone; for non-steroidal anti-inflammatory agents (NSAIDs), include diflunisal, ibuprofen, and ketoprofen; for local anesthetics, include chloroprocaine hydrochloride, lidocaine hydrochloride, and procaine hydrochloride; for analgesics and analgesic combinations, include: acetaminophen, aspirin, and salicylates.

It should be appreciated that one or more of these and other drugs described herein exist in many pharmaceutically acceptable salts. Examples for such salts include those generated by using inorganic agents (i.e., inorganic cations such as sodium, potassium, calcium, etc. and inorganic anions such as chloride, bromide, etc.) and organic agents (i.e., organic cations such as piperazinyl, triazinyl, etc., and organic anions such as citrates, tartrates, tosylates, etc.).

In addition, these drugs may be present as polymorphs, or isomers, or both. Examples for polymorphs include monohydrates, dihydrates, hemi-hydrates, etc., as well as the high-melting and low-melting polymorphs. These polymorphs can be characterized using X-ray techniques or other techniques well known in the art. Examples of isomers include geometric and optical isomers.

Furthermore, the pharmaceutical art has recognized that such salts, isomers, and polymorphs, as well as the prodrugs (the drugs prior to being metabolized), analogs thereof, or metabolites therefrom can be therapeutically effective as well and thus can be substituted with ease. Examples for other drugs for use with the present invention may be found in the U.S. Pat. No. 5,656,286, which is incorporated by reference in its entirety.

In one specific aspect, the drug may be a fluconazole, its salts, analogs, isomers, derivatives, prodrugs, or metabolites, or mixtures or combinations thereof.

In general, cosmeticeuticals achieve a positive or beautifying effect upon the appearance of a nail and its surrounding tissue by imparting a beneficial action, which improves the health, of the nail and its surrounding tissue. Examples for cosmeceuticals include, without limitation, vitamins, minerals, antioxidants, amino acids, peptides, depigmenting agents (including sulfites, bisulfites and metabisulfites; alkaline earth and alkaline earth metal compounds thereof), as well their analogs, derivatives, and mixtures thereof.

Furthermore, substances such as moisturizers, peptides, proteins, carbohydrates, and fats, etc., that are known to exert positive benefits which in turn results in an improvement in appearance of the nail, when administered, may be used as cosmeticeuticals. Other substances that may be beneficial for inclusion in the present nail composition, such as cosmetic additives which are not recited but well known to those in the cosmetics arts, may be included herein.

In one aspect of the present invention, the cosmeticeutical may be a vitamin analog. In another aspect, the vitamin analog may be a retinoid. In a further aspect, the retinoid may be a trans retinoic acid, 13-cis retinoic acid, as well as their salts, derivatives, analogs, prodrugs, metabolites, and mixtures thereof.

It is appreciated that the above categories of drugs and cosmeticeuticals are not rigidly described and that a drug or cosmeticeutical may be described accurately in more than one category or sub-category. For example, diclofenac may be described as an analgesic, as well as an anti-inflammatory.

In accordance with the present invention the nail agents are used in an amount of from about 0.1% w/w to about 30% w/w of the composition. In another aspect of the invention, the nail agents are used in an amount of from about 0.5% w/w to about 25% w/w of the composition. In yet another aspect of the invention, the nail agents are used in an amount of from about 1% w/w to about 20% w/w of the composition.

In accordance with the Definition section, a concentration range of about 0.1% to about 30% should be interpreted to include not only the explicitly recited concentration limits of from about 0.1% w/w to about 30%, but also to include individual concentrations such as 0.5% w/w, 1% w/w, 3% w/w, 5% w/w, 6% w/w, 8% w/w, 10% w/w, 14% w/w, 15% w/w, 18% w/w, 20% w/w, 24% w/w, 25% w/w, 27% w/w, 30% w/w, and sub-ranges such as 0.1% w/w to 0.9 w/w, 1% w/w to 3% w/w, 2% to 4% w/w, 3% to 5% w/w, 4% to 6% w/w, etc. The same principle applies to the following ranges: of about 1% to about 15% w/w; of about 2 to 6% w/w; and of about 6% to about 16% w/w.

Non-cellulosic Polymeric Carriers

The nail composition of the present invention comprises a non-cellulosic polymeric carrier. Such a carrier includes vinyl polymers and copolymers including cross-linked and uncross-linked vinyl polymers and copolymers; natural biopolymers and synthetic polymers, such as non-cellulosic resins and gums, natural and synthetic rubbers and block copolymer rubbers including polyisobutylenes, neoprenes, polybutadienes, polyisoprenes and styrene block copolymers (e.g., SBS) of the above; ethylenevinylacetate copolymers; polysiloxanes; polyacrylates; polyurethanes; plasticized weight polyether block amide copolymers, and plasticized styrene-rubber block copolymers; or mixtures thereof.

The vinyl polymeric carrier comprises polyvinyl acetates, partially hydrolyzed polyvinyl acetates, copolymers of vinyl acetate and acrylic acid, copolymers of vinyl acetate and crotonic acid, copolymers of vinyl acetate and a monoalkyl maleate, ternary copolymers of vinyl acetate, crotonic acid, and vinyl neodecanoate, ternary copolymers of vinyl acetate, crotonic acid, and vinyl propionate, copolymers of a methylvinyl ether, and a monoalkyl maleate, copolymers of a fatty acid vinyl ester and acrylic acid or methacrylic acid, ternary copolymers of N-vinylpyrrolidone, methacrylic acid, and an alkyl methacrylate, copolymers of acrylic acid and methacrylic acid, copolymers of acrylic acid and an alkyl acrylate, copolymers of acrylic acid and an alkyl methacrylate, polyvinyl acetal, polyvinyl butyral, alkyl-substituted poly-N-vinylpyrrolidones, alkyl esters of a copolymer of an olefin and maleic anhydride, and any mixture thereof.

In one aspect, the polymeric carrier comprises a copolymer of methylvinyl ether and either maleic acid or maleic anhydride. Such resin polymers are sold under the trade name GANTREZ® by ISP Corp., Wayne, N.J., U.S.A.

In another aspect of the present invention, the polymeric carrier may comprise from about 50–99% w/w of the composition. In another aspect, the carrier comprises from about 60% to about 99% w/w of the composition. In yet another aspect, the carrier comprises from about 70% to about 99.5% w/w of the composition.

In accordance with the Definition section, a concentration range of about 50 to about 99% w/w should be interpreted to include not only the explicitly recited concentration limits of about 50% w/w to about 99%, but also to include individual concentrations such as 50% w/w, 55% w/w, 60% w/w, 65% w/w, 70 w/w, 75% w/w, 80% w/w, 85% w/w, 90% w/w, 95% w/w, etc., and sub-ranges such as from about 50% w/w to 52% w/w, from about 51% w/w to 53% w/w, from about 52% to 54% w/w, from about 53% to 55% w/w, from about 54% to 56% w/w, etc.

Enhancers

As discussed in the Background section, the enhancers of the prior art are reducing or kerolytic agents composed of urea, sulfhydryl-containing amino acids, or thioglycolate, or combinations thereof. The enhancers of the present invention are distinct from those taught in the prior art because they are devoid of urea, sulfhydryl-containing amino acid, or thioglycolate. The enhancers of the present invention are also devoid of vasolidators, which are also taught for use in nail treatment by the prior art.

Examples of suitable enhancers of the present invention include, but are not limited thereto: fatty acids, fatty acid esters, fatty alcohols, fatty acid esters of lactic acid or glycolic acid and their salts, amides, amines, pyrrolidones, glycerol triesters, terpenes, classicial surfactants, azocyclic compounds, organic acids, complexing agents, biologics and mixtures thereof.

In one aspect of the present invention, the enhancer may be a fatty acid. Examples of acceptable fatty acids include, but are not limited thereto, oleic acid, alkanoic acids, caproic acid, hexanoic acid, lactic acid, lauric acid, linoleic acid, and mixtures thereof.

In another aspect of the present invention, the enhancer may be a fatty acid ester. Examples of acceptable fatty acid esters include, but are not limited thereto, methyl laurate, glycerol monooleate (GMO), sorbitan monooleate (SMO), glycerol monolaurate (GML), glycerol monolinoleate (GMLO), isopropyl myristate, isopropyl palmitate, methyl propionate, monoglycerides, propylene glycol monolaurate, sorbitan monolaurate, and mixtures thereof.

In a further aspect of the present invention, the enhancer may be a fatty alcohol. Examples of fatty alcohols include, but are not limited thereto, lauryl alcohol, caprylic alcohol, myristyl alcohol, cetyl alcohol, aliphatic alcohols, linolenyl alcohol, nerolidol, oleyl alcohol, and mixtures thereof.

In yet another aspect of the present invention, the enhancer may be a fatty acid ester of lactic acid or glycolic acid. Examples of fatty acid esters of lactic acid or glycolic acid or their salts include, but are not limited thereto, lauroyl glycolate, sodium lauryol glycolate, caproyl glycolate, sodium caproyl glycolate, cocyl glycolate, sodium cocyl glycolate, isostearoyl glycolate, tromethamine lauroyl glycolate, lauroyl lactylate, sodium lauroyl lactylate, caproyl lactylate, sodium caproyl lactylate, cocoyl lactylate, sodium cocyl lactylate, isostearoyl lactylate, tromethamine lauryol lactylate, and mixtures thereof.

In another aspect of the present invention, the enhancer may be an amide. Examples of amides include, but are not limited to, lauramide diethanolamide, alkanolamides, ethoxylated alkanolamides, ethylene bisamides, and mixtures thereof.

In another aspect of the present invention, the enhancer may be a pyrrolidone. Specific acceptable pyrrolidones include, but are not-limited thereto, N-methyl-pyrrolidone N-alkyl-pyrrolidones, pyrrolidone carboxylic acids, pyrrolidone carboxylic esters, and mixtures thereof.

In another aspect of the present invention, the enhancer may be a glycerol triester. Examples of glycerol triesters include, but are not limited thereto, triacetin, diacetin, monoacetin, tributylrin, tricaproin, tricaprylin, trilaurin, trymyristin, tripalmitin, tristearin, triethyl citrate, tributyl citrate, and mixtures thereof.

In a further aspect of the present invention, the enhancer may be a terpene. Examples of terpenes include, but are not limited thereto, lemonene, methone, pipertone, 1–8 cineole, terpineol, terpinen-4-ol pulegone, carvone, carveol, and mixtures thereof.

In another aspect of the present invention, the enhancer may be an amine. Specific examples of acceptable amines include, but are not limited thereto, lauryl-amine (dodecylamine), and mixtures thereof.

In another aspect of the present invention, the enhancer may be an azo compound or azocyclic compound. Examples of azo compounds include, but are not limited thereto, azone.

In an additional aspect of the present invention, the enhancer may be a classical surfactant. Examples of classical surfactants include, but are not limited thereto, polyoxyethylene surfactants having 2–100 alkyl ethers, known commercially as Brij surfactants, (such as Brij 30, Brij 36T, Brij, 35, Brij 52), polyoxyethylene block polymer type surfactants, known commercially as Pluronic surfactants, (such as Pluronic F68, and Pluronic L62), sorbitan fatty acid ether type surfactants, known commercially as Span surfactants, (such as Span 20 and Span 85), and polyoxyethylene sorbitan fatty acid ether type surfactants, known commercially as Tween surfactants, (Such as Tween 20, Tween 40, and Tween 80), Poloxomer surfactants, Myrj surfactants, bile acids and their salts, sodium laurate, sodium lauryl sulfate, and mixtures thereof.

In a further aspect of the present invention, the enhancer may be a complexing agent. Examples of acceptable complexing agents include, but are not limited thereto, EDTA salts and mixtures thereof.

In another aspect of the present invention, the enhancer may be an organic acid. Examples of organic acids include, but are not limited thereto, salicylic acid, citric acid, salicylates, and mixtures thereof.

In yet another aspect of the present invention, the enhancer may be a biologics. Examples of biologics include, but are not limited thereto, L-α-amino acids, lecithin, phospholipids, and mixtures thereof.

In a further aspect of the invention, the enhancer may be triacetin, lauramide diethanolamine, 1,8-epoxy-p-menthane caproic triglyceride, cineole, dimethylsulfoxide (DMSO), dimethyl formamide (DMF), or N,N-dimethylacetamide (DMA), or any mixtures thereof.

In addition to the enhancer substances enumerated above, many natural substances are capable of acting as permeation enhancers as well. These natural substances include, but are not limited thereto, arecoline, berbamine, berberine, camphol, capsaicin, capsaicine, capsic acid, eucalyptus (oil), eucalyptols, ferulic acid, menthol, oleummenthae, paeonol, peppermint oil, and mixtures thereof.

In accordance with the present invention, the nail enhancer substances enumerated above are used in an amount of from about 0.1 to about 30% w/w of the composition. In one aspect, the enhancer may comprise from about 0.5 to about 20% w/w of the composition. In yet another aspect, the enhancer may comprise from about 0.5 to 10% of the composition.

In accordance with the Definition section, a concentration range of about 0.1 to about 30% w/w should be interpreted to include not only the explicitly recited concentration limits of 0.1% w/w to about 30%, but also to include individual concentrations such as 0.2% w/w, 0.5% w/w, 1% w/w, 2% w/w, 4%w/w, 5% w/w, 7% w/w, 8% w/w, 10%w/w, 15% w/w, and sub-ranges such as from about 0.1% w/w to 0.9% w/w, from about 1% w/w to 3% w/w, from about 2% to 4% w/w, from about 3% to 5% w/w, from about 4% to 6% w/w, etc. The same principle applies to the following ranges: from about 1% to about 10%; from about 1 to 5% w/w; and any ranges narrower or larger than these ranges.

In accordance with the present invention, the permeation rate of a nail agent across the nail plate ranges from about 0.1 to about 250 $\mu g/cm^2$/week, from about 1 to about 200 $\mu g/cm^2$/week, and from about 1 to 150 $\mu g/cm^2$/week. The ranges of the permeation rate from about 0.1 to about 250 $\mu g/cm^2$/week should be interpreted to include not only the explicitly recited rates of from about 0.1 to about 250 $\mu g/cm^2$/week, from about 1 to 200 $\mu g/cm^2$/week, or from about 1 to 150 $\mu g/cm^2$/week, but also to include individual rates such as 0.1 $\mu g/cm^2$/week, 0.5 $\mu g/cm^2$/week, 1.0 $\mu g/cm^2$/week, 10.0 $\mu g/cm^2$/week, 100 $\mu g/cm^2$/week, 150 $\mu g/cm^2$/week, 200 $\mu g/cm^2$/week, etc., and sub-ranges such as from about 0.1 to 1.0 $\mu g/cm^2$/week, from about 0.5 to 1.5 $\mu g/cm^2$/week, from about 1.0 to 10 $\mu g/cm^2$/week, from about 10 to 20 $\mu g/cm^2$/week, from about 15 to 30 $\mu g/cm^2$/week, from about 30 to 100 $\mu g/cm^2$/week, from about 50 to 200 $\mu g/cm^2$/week, from about 75 to 250 $\mu g/cm^2$/week, etc. The same principle applies to the ranges of from about 1 to 200 $\mu g/cm^2$/week, and from about 1 to 150 $\mu g/cm^2$/week.

Associated Methods

Where desired, the nail compositions of the present invention as described herein maybe applied following treatment of the nails with a pre-treatment composition. The pre-treatment composition may cleanse the area to be applied and may also improve nail flux of a given agent. The pre-treatment composition comprises a polyalcohol, a fatty acid ester, or a mixture thereof. The pretreatment composition may include agents such as propylene glycol, sorbitan monooleate, and N-methyl pyrrolidone, and other enhancers and mixtures thereof.

Other pretreatment compositions can be prepared and used with ease by one of skill in the art, upon reading this disclosure. In one aspect, the polyalcohol or fatty acid ester comprises from about 0.5% to about 30% w/w of the pre-treatment composition. This concentration range of about 0.5 to about 30% w/w should be interpreted to include not only the explicitly recited concentration limits of about 0.5% to about 30% w/w, but also to include individual concentrations such as 0.8% w/w, 1% w/w, 4% w/w, 5% w/w, 6% w/w, 7% w/w, 8% w/w, 9% w/w, 10%w/w, 11% w/w, 12% w/w, 13% w/w, 14%w/w, 15% w/w, 16%w/w, 17% w/w, 18% w/w, 19% w/w, 20% w/w, 21% w/w, 22%w/w, 23% w/w, 24% w/w, 25% w/w, etc., and sub-ranges such as from about 0.5% w/w to 1.5% w/w, from about 3% w/w to 5% w/w, from about 4% to 6% w/w, from about 5% to 7% w/w, from about 6% to 8% w/w, etc.

In another aspect of the invention, the pre-treatment composition may not comprise an enhancer when it is used in association with a nail composition already comprising an enhancer. Alternatively, the pre-treatment composition may comprise an enhancer when used in association with a nail composition that does not comprise an enhancer. By using the present compositions and the administration methods, the nail flux of a nail agent can be enhanced.

The nail composition of the present invention may take a variety of delivery formulations, including but not limited to topical formulations, such as gels, foams, ointments, aerosols, creams, lacquers, powders, and solutions. Further, the composition may be used in connection with a delivery structure, such as a bandage, which is adapted to administer the composition to the nail.

In general, the composition is administered and the surface composition is allowed to dry. Solvents for use with the present invention include, but not limited thereto, acetone, acetyl triethyl citrate, alcohol, t-amyl alcohol, benzyl benzoate, bornyl acetate, butyl alcohol, t-butyl alcohol, chloroform, diethylene glycol dibutyl ether, diethylene glycol dimethyl ether, dimethyl isosorbide, dimethyl sulfoxide, dioctyl adipate, Dioctyl phthalate, 1,4-Dioxane, ethyl acetate, ethoxydiglycol, ethylene glycol dimethyl ether, glycereth-7 triacetate, hexylene glycol, isopropyl alcohol, isostearyl lactate, isopropyl palmitate, methyl alcohol, methyl t-butyl ether, methylene chloride, methyl gluceth-10, methyl gluceth-20, methyl isobutyl ketone, N-methyl-2- pyrrolidone, PEG-4 dimethyl ether, PEG-6 isostearate, PEG-8 palmitostearate, PEG-150 palmitostearate, 3-pentanol, phenethyl alcohol, β-picoline, γ-picoline, polyethylene glycol, polyethylene glycol monomethyl ether; Polyglyceryl-3 diisosteaerate, polypropylene glycol, PPG-10 butanediol, PPG-10 methyl glucose ether, PPG-20 methyl glucose ether, PPG-15 staryl ether, propylene glycol, propylene glycol dicaprylate/dicaprate, propylene glycol laurate, 2-pyrrolidone, SDA alcohol 3A, α-terpineol, and tetrahydrofuran.

In addition to the nail agent, an enhancer, and a polymeric carrier, the present invention may comprise a number of additives such as diluents, excipients, emollients, plasticizers, or mixtures thereof. These, as well as other additives not specifically recited, are well known in the art and may be added to the nail composition of the present invention in specific types and amounts as needed.

EXAMPLES

The following examples are intended to be merely illustrative of the various aspects of the present invention disclosed herein and are not intended in any ways to limit the scope of the claimed invention. Other aspects of the invention that are considered equivalent by those skilled in the art are also within the scope of this invention.

Nail Flux Methodology

The general methods for determining the in vitro nail flux are known in the art. See, for example, U.S. Pat. No. 5,696,164, and references cited therein.

In vitro human cadaver nail flux studies were conducted using modified Franz non-Jacketed permeation cells. The temperature of the nail surface was maintained at 32° C. by placing the cells in a circulating water bath positioned over a stirring module. Human fingernails or toenails were stored under frozen conditions in 0.02% (w/v) sodium azide solution or selected receiver medium. Nails that were greater than 1 cm² in area were used for the flux studies. Nails with dorsal side facing the donor compartment were sandwiched between two layers of a closed cell polyethylene foam film. Annular ring of 2.38 cm outer diameter and 0.95 cm inner diameter was cut from the backinig film. The area of the donut hole (0.97 cm²) is large enough to provide complete contact with the receiver media. The purpose of the foam backing film was to prevent any leakage of receiver medium from the cell assembly. The nails were allowed to hydrate at 32° C. overnight with 0.02% (w/v) sodium azide solution in the receiver compartment.

The following morning, nail lacquer sufficient to cover the nail surface was placed onto the dorsal side of the nail. Alternatively, a fixed amount of the lacquer can also be used. Each nail was then loaded between the donor and receiver compartments of a diffusion cell, with the ventral side of nail facing the receiver compartment, and clamped in place. The duration of nail flux and retention study varied from 3 days to 3 weeks. At predetermined sampling intervals, the entire contents of the receiver compartment were collected for drug quantitation and the receiver compartment was filled with fresh receiver solution, taking care to eliminate any air bubbles at the skin/solution interface.

The cumulative amount of drug permeated per unit area at any time t ($Q_t$, μg/cm²) was determined as follows:

$$Q_t = \sum_{n=0}^{t} (C_n * V) / A$$

where $C_n$ is the concentration (μg/ml) of the drug in the receiver sample for the corresponding sample time, V is the volume of fluid in the receiver chamber (~1.63 cm³), and A is the diffusion area of the cell (0.64 cm²).

Example I

The solids content of Gantrez® polymer solution was determined by weighing a small amount of the solution in a pre-weighed aluminum dish. The solvent was evaporated by overnight drying in a convection oven maintained at 70° C. and the percent of solids content was determined from the ratio of final dried weight to the initial solution weight.

A known amount of the Gantrez® polymer solution was weighed into a glass bottle. From the weight of the Gantrez® polymer solution and the percent of solids content, the amount of solid in the solution was calculated. Appropriate quantities of the drug and other excipients (e.g. solvents, enhancers) were added to yield the desired compositions. The glass bottle was then tightly capped, sealed with parafilm, and rotated overnight until all ingredients had completely dissolved and the nail lacquer solution was visually clear.

| Formulation | Composition (%, w/w) | $Q_t$ (t = 1 week) (μg/cm²t)* |
|---|---|---|
| Gantrez ES-335/FLC | 85/15 | 12.2 |
| Gantrez ES-335/FLC/Triacetin | 82/15/3 | 26.6 |
| Gantrez ES-335/FLC/Triacetin | 80/15/5 | 28.4 |

Gantrez ® ES-335: n-isopropyl monoesters of poly (methyl vinyl ether/maleic acid) in IPA; FLC: Fluconazole.
*(Mean), n = 3 nail donors, 6 nail plates.

These data show that nail flux of fluconazole has been enhanced by about 100% by using 3–5% triacetin.

Using the general method described above, nail compositions described in Examples II–V were prepared with the corresponding formulae shown in the relevant Tables.

Example II

| Formulation | Composition (%, w/w) | $Q_t$ (t = 1 week) (μg/cm²t)* |
|---|---|---|
| Gantrez ES-335/FLC | 91/9 | 18.3 |
| Gantrez ES-335/FLC/L-DEA | 86/9/5 | 25.3 |

Gantrez ® ES-335: n-isopropyl monoesters of poly (methyl vinyl ether/maleic adid) in IPA; FLC: Fluconazole; L-DEA: Lauramide Diethanolamine (DEA).
*(Mean), n = 3 nail donors, 6 nail plates.

These data show that L-DEA (5%) gives about 40% increase in flux rate.

Example III

| Formulation | Composition (%, w/w) | $Q_t$ (t = 1 week) (μg/cm²t)* |
|---|---|---|
| Gantrez ES-335/FLC | 91/9 | 22.9 |
| Gantrez ES-335/FLC/Cineole | 86/9/5 | 48.9 |
| Gantrez ES-335/FLC/TCP | 86/9/5 | 36.3 |

Gantrez ® ES-335: n-isopropyl monoesters of poly (methyl vinyl ether/maleic acid) in IPA; FLC: Fluconazole; Cineole: Eucalyptol (1,8-epoxy-p-menthane); TCP: Tricaproin (Caproic triglyceride).
*(Mean), n = 5 nail donors, 10 nail plates.

These data show that Cineole (5%) provides about 100–125% increase in flux rate. On the other hand, TCP (5%) provides a flux rate increase of about 60%. Again, depending on the desired drug loading and release rates, one may select the appropriate carrier and enhancer.

Example IV

In the following example, all nail plates were pre-treated with the following solutions containing enhancers or no enhancer for 72 hours before the nail flux studies.

Control Solution: Ethanol/H2O=50/50 (%, v/v)

Solution 1: Ethanol/H2O/Propylene Glycol=45/50/5 (%, v/v)

Solution 2: Ethanol/H2O/Sorbitan Monooleate=45/50/5 (%, v/v)

| Pre-Treatment | Formulation | Composition (%, w/w) | $Q_t$ (t = 1 week) ($\mu g/cm^2 t$)* |
|---|---|---|---|
| Control Solution | Gan. ES-335/FLC | 91/9 | 2.6 |
| Solution 1 | Gan. ES-335/FLC | 91/9 | 8.7 |
| Solution 2 | Gan. ES-335/FLC | 91/9 | 6.1 |

Gan. = Gantrez ® ES-335: n-isopropyl monoesters of poly (methyl vinyl ether/maleic acid) in IPA; FLC: Fluconazole.
*(Mean), n = 3 nail donors, 6 nail plates.

These data show that pre-treatment with a pretreatment composition has dramatically increased the flux rate by about 300%.

Example V

In the following example, all nail plates were pretreated with the following solutions containing enhancers or no enhancer for 72 hours before the nail flux studies.

Control solution: Ethanol/H2O=50/50 (%, v/v),

Solution 1: Ethanol/H2O/N-Methyl Pyrrolidone=35/50/15 (%, v/v)

| Pre-Treatment | Formulation | Composition (%, w/w) | $Q_t$ (t = 1 week) ($\mu g/cm^2 t$)* |
|---|---|---|---|
| Control Solution | Gan. ES-335/FLC | 91/9 | 7.2 |
| Solution 1 | Gan. ES-335/FLC | 91/9 | 12.3 |

Gan. = Gantrez ® ES-335: n-isopropyl monoesters of poly (methyl vinyl ether/maleic acid) in IPA; FLC: Fluconazole.
*(Mean), n = 3 nail donors, 6 nail plates.

These data show that pretreatment with an N-methyl-pyrrolidone composition has increased the flux rate of fluconazole by about 70%. This is also a significant result.

In summary, pretreatment improves flux rate dramatically, even where the nail composition comprises no enhancer other than alcohol which is used as a solvent in both control solution and solutions added with a pre-treatment chemical. From this data, a nail composition with an enhancer of the present invention, coupled with a pretreatment composition is expected to provide additive or synergistic results. Accordingly, such compositions are also within the scope of this invention.

Not to be bound by theory, the synergistic effect, as observed in the present invention, may result from the positive interaction between a solvent and an enhancer, an interaction between solvent and another solvent, or an interaction between an enhancer and another enhancer, or an interaction between or among any of the enhancers and solvents.

The above-described compositions and methods are only illustrative of the application of the principles of the present invention. Modifications and alternative compositions and methods may be devised by those skilled in the art without departing from the spirit and scope of the present invention and the appended claims are intended to cover such modifications and alternatives. Thus, while the present invention has been described above with particularity and detail in connection with what is presently deemed to be the most practical and preferred embodiments of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A nail composition comprising an antifungal agent, a vinyl polymeric or vinyl copolymeric carrier, and an enhancer, wherein the enhancer comprises a member selected from the group consisting of triacetin, lauramide diethanolamine, caproic triglyceride, cineole, and any combinations thereof, and wherein said nail composition is substantially free of any member selected from the group consisting of urea, sulfhydryl-containing amino acids, and vasodilators.

2. The nail composition of claim 1 wherein the antifungal agent is a member selected from the group consisting of an azole, an allyl compound, and any combinations thereof.

3. The nail composition of claim 2 wherein the antifungal agent is a triazole or an imidazole.

4. The nail composition of claim 3 wherein the antifungal agent is fluconazole.

5. The nail composition of claim 1 wherein the concentration of the antifungal agent is from about 0.1 to 30% by weight of the composition.

6. The nail composition of claim 1 wherein the concentration of the antifungal agent is from about 1 to 20% by weight of the composition.

7. The nail composition of claim 1 wherein the concentration of the enhancer is from about 0.1 to about 30% by weight of the composition.

8. The nail composition of claim 1 wherein the concentration of the enhancer is from about 0.5 to about 20% by weight of the composition.

9. The nail composition of claim 1 wherein the concentration of the enhancer is from about 1 to about 10% by weight of the composition.

10. The nail composition of any of claims 1–9 wherein the carrier comprises a copolymer of methylvinyl ether and maleic acid or a copolymer of methylvinyl ether and maleic anhydride.

11. A method for enhancing the nail flux of an antifungal agent in a nail composition, said method comprising providing to said composition an enhancer, said enhancer comprising a member selected from the group consisting of triacetin, lauramide diethanolamine, caproic triglyceride, cineole, and any combinations thereof.

12. A method for enhancing the nail flux of an antifungal agent in a nail composition, said method comprising, prior to administering said composition to a nail surface, administering to said nail surface a pre-treatment composition, comprising an enhancer selected from the group consisting of: triacetin, lauramide diethanolamine, caproic triglyceride, cineole, and combinations thereof.

13. A method for treating or ameliorating a nail condition of a subject, comprising administering to an affected nail of the subject the nail composition of claim 1.

14. A method for treating or ameliorating a nail condition of a subject, comprising the method of claim 12.

15. A nail kit comprising the nail composition of claim 1 and further comprising a pre-treatment composition 16. The nail kit of claim 15 wherein the pre-treatment composition further comprises an enhancer.

17. The nail kit of claim 16 wherein the enhancer of the pre-treatment composition comprises a member selected from the group consisting of triacetin, lauramide diethanolamine, caproic triglyceride, cineole, and any combinations thereof.

18. A bandage adapted for the topical administration of the nail composition of claim 1 to a nail.

19. The nail composition of claim 1, wherein the enhancer is triacetin.

20. The nail composition of claim 1, wherein the enhancer is lauramide diethanolamine.

21. The nail composition of claim 1, wherein the enhancer is caproic triglyceride.

22. The nail composition of claim 1, wherein the enhancer is cineole.

* * * * *